(12) United States Patent
Worley, III

(10) Patent No.: US 10,993,025 B1
(45) Date of Patent: Apr. 27, 2021

(54) ATTENUATING UNDESIRED AUDIO AT AN AUDIO CANCELING DEVICE

(71) Applicant: Amazon Technologies, Inc., Seattle, WA (US)

(72) Inventor: William Spencer Worley, III, Camano Island, WA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 16/289,446

(22) Filed: Feb. 28, 2019

Related U.S. Application Data

(63) Continuation of application No. 14/824,815, filed on Aug. 12, 2015, now abandoned, which is a
(Continued)

(51) Int. Cl.
*H04R 3/00* (2006.01)
*G10L 15/00* (2013.01)
*G10K 15/02* (2006.01)

(52) U.S. Cl.
CPC .................................. *H04R 3/002* (2013.01)

(58) Field of Classification Search
CPC ........ G01K 15/02; G01K 15/10; G01K 15/12; G01K 2200/10; G01K 2210/106; G01K 2210/108; G01K 2210/1081; G01K 2210/1082; G01K 2210/111; G01K 2210/112; G01K 2210/114; G01K 2210/117; G01K 2210/12; G01K 2210/123; G01K 2210/128; G01K 2210/1281; G01K 2210/1282; G01K 2210/1283; G01K 2210/1291; G01K 2210/3012; G01K 2210/3013; G01K 2210/3014; G01K 2210/3016; G01K 2210/3018; G01K 2210/3022; G01K 2210/3023; G01K 2210/3026; G01K 2210/3028; G01K 2210/3029; G01K 2210/3035; G01K 2210/3036; G01K 2210/3038; G01K 2210/3043; G01K 2210/3044; G01K 2210/3045; G01K 2210/3047; G01K 2210/3048; G01K 2210/3053; G01K 2210/03; G01K 11/16; G01K 11/00; G01K 11/178; G01K 11/002; G01K 11/1782; G01K 2200/12; G01K 2200/3215; H04R 2201/34; H04R 2203/12; H04R 2430/21;
(Continued)

(56) References Cited

U.S. PATENT DOCUMENTS 5,267,320 A * 11/1993 Fukumizu ............ G10K 11/178
381/71.12
5,377,276 A   12/1994 Terai et al.
(Continued)

*Primary Examiner* — Leshui Zhang
(74) *Attorney, Agent, or Firm* — Athorus, PLLC

(57) ABSTRACT

The implementations described include an audio canceling device that receives and audio signal from within an environment, identifies desired and undesired audio from the received audio signal and generates an attenuation-signal for use in canceling out or reducing the volume of the undesired audio at a canceling location. In addition, the audio canceling device, may determine a time delay before the attenuation-signal should be transmitted from an output based on a distance between the undesired audio source location and the canceling location and a distance between the output and the canceling location.

20 Claims, 11 Drawing Sheets

Related U.S. Application Data continuation of application No. 13/529,326, filed on Jun. 21, 2012, now Pat. No. 9,111,522.

(58) Field of Classification Search
CPC ............ H04R 2430/23; H04R 2430/25; H04R 3/002; H04R 3/02; H04R 1/347; H04R 2410/00; H04R 2410/01; H04R 2410/03; H04R 2410/05; H04R 2410/07; H04R 2460/01; H04N 5/9202; H04N 5/9203; H04N 5/9204; H04N 5/9265; H04N 5/9267; H04N 5/928; H04N 7/04; H04N 7/045; H04N 9/802; H04N 9/8085; H04N 9/8087; H04N 9/8088; H04N 9/8211; H04N 9/8216; H04N 9/8222; H04N 9/8255; H04N 9/835; H04N 9/8355; G10L 15/00–075
USPC .... 381/71.1–71.12, 73.1, 74, 77, 79, 80, 81, 381/82, 86, 92, 93, 94.1, 94.7, 95, 97, 56, 381/57, 59, 94.9; 455/569.2, 570, 114.2, 455/63.1; 704/E21.014, 231–257; 379/406.03, 406.5, 406.6, 406.07, 406.08, 379/406.9, 406.1, 406.11; 700/94; 348/484, E07.001

See application file for complete search history.

(56) References Cited

U.S. PATENT DOCUMENTS

| | | |
|---|---|---|
| 5,815,582 A * | 9/1998 | Claybaugh ........... G10K 11/178 381/71.6 |
| 6,654,467 B1 | 11/2003 | York et al. |
| 7,716,376 B1 | 5/2010 | Price et al. |
| 8,275,145 B2 | 9/2012 | Buck et al. |
| 8,611,552 B1 | 12/2013 | Murgia et al. |
| 2002/0141599 A1 | 10/2002 | Trajkovic et al. |
| 2007/0280486 A1 | 12/2007 | Buck et al. |
| 2008/0188271 A1 | 8/2008 | Miyauchi |
| 2010/0014685 A1 * | 1/2010 | Wurm ............... G10K 11/17881 381/71.11 |
| 2010/0124336 A1 | 5/2010 | Shridhar et al. |
| 2010/0146115 A1 | 6/2010 | Bezos |
| 2010/0177905 A1 | 7/2010 | Shridhar et al. |
| 2010/0208911 A1 | 8/2010 | Maeda et al. |
| 2010/0290635 A1 | 11/2010 | Shridhar et al. |
| 2011/0243344 A1 * | 10/2011 | Bakalos ................ G10K 11/178 381/71.6 |
| 2012/0069242 A1 * | 3/2012 | Pearlstein ............ G10K 11/178 348/484 |
| 2012/0177213 A1 | 7/2012 | Faucheur |
| 2013/0156212 A1 * | 6/2013 | Bjelosevic ........ G10K 11/17823 381/71.1 |
| 2013/0182865 A1 | 7/2013 | Paul |

* cited by examiner

US 10,993,025 B1

ATTENUATING UNDESIRED AUDIO AT AN AUDIO CANCELING DEVICE

CROSS-REFERENCE TO RELATED APPLICATIONS

This application is a continuation of and claims priority to U.S. patent application Ser. No. 14/824,815, filed Aug. 12, 2015, titled "Selective Audio Canceling," which is a continuation of and claims priority to U.S. patent application Ser. No. 13/529,326, filed Jun. 21, 2012, titled "Selective Audio Canceling," the contents of which are incorporated by reference herein in their entirety.

BACKGROUND

Homes are becoming more wired and connected with the proliferation of computing devices such as desktops, tablets, entertainment systems, and portable communication devices. As these computing devices evolve, many different ways have been introduced to allow users to interact and communicate with those devices and with each other, such as through mechanical devices (e.g., keyboards, mice, etc.), touch screens, motion detectors, voice control and gesture recognition systems.

One drawback with an increased number of computing devices is the added noise present in a room that is generated by those devices and/or the people using those devices. For example, if there are two people in a room, one talking on a telephone and one watching television, it may be difficult for the person watching television to hear the television audio due to the added noise from the person talking on the telephone.

BRIEF DESCRIPTION OF THE DRAWINGS

The detailed description is described with reference to the accompanying figures. In the figures, the left-most digit(s) of a reference number identifies the figure in which the reference number first appears. The use of the same reference numbers in different figures indicates similar or identical components or features.

DETAILED DESCRIPTION

Figure 1:
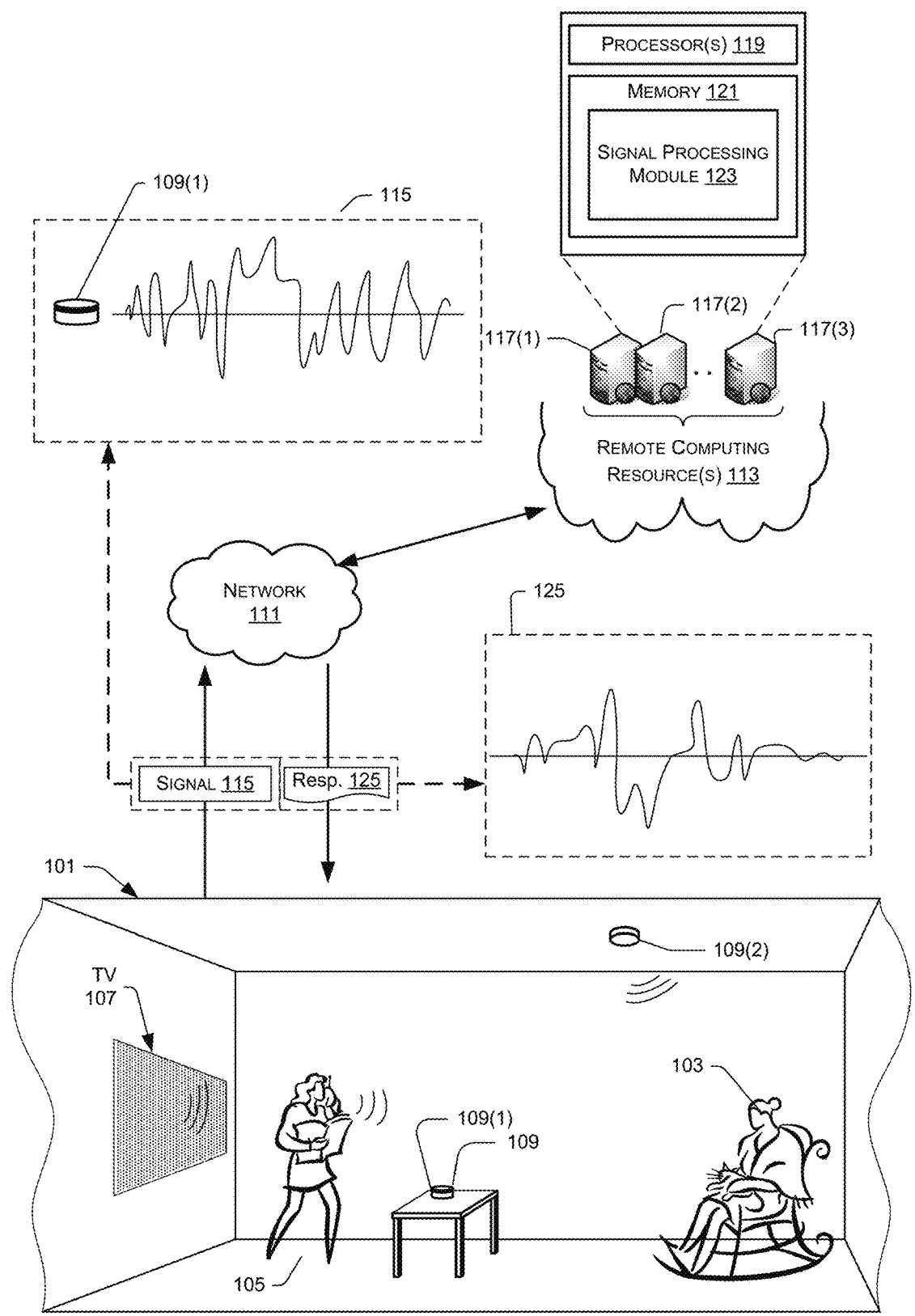
FIG. 1 depicts an example audio canceling computing architecture set in an example home environment.

This disclosure describes, in part, computing devices that receive audio signals from sound waves within an environment, identify desired and undesired audio and cancel out the undesired audio at a canceling location so a person at the canceling location can receive the desired audio. For example, if two people are in a room, one is talking on the phone (undesired audio) and one is watching television (desired audio), a computing device may receive an audio signal carried on sound waves within the room and identify the audio signal generated from the person talking on the phone (undesired audio signal) and the audio signal produced by the television (desired audio signal). The computing device may then generate an attenuation-signal by, for example, phase shifting and/or inverting the polarity of the undesired audio signal. That attenuation-signal may then be amplified and a sound wave (attenuation-sound wave) transmitted that is directly proportional to the amplitude of the original sound wave carrying the undesired audio signal, thereby creating destructive interference. The transmission of the attenuation-sound wave may be timed so that its arrival at the canceling location (e.g., location of a person watching the television) will coincide with the arrival of the sound wave carrying the undesired audio signal. By timing the arrival of the attenuation-sound wave carrying the attenuation-signal to coincide with the arrival of the sound wave carrying the undesired audio signal, the destructive interference will effectively reduce the volume of the undesired audio while leaving the desired audio intact.

While the examples described below utilize a single audio canceling device, it will be appreciated that multiple audio canceling devices, multiple audio transducers and/or multiple outputs may be utilized alone or in combination. Each of these audio canceling devices may include one or more audio transducers, such as a microphone, for receiving audio signals and one or more output devices for transmitting audio signals (e.g., speakers). In some examples, the audio canceling devices may include a scenario of multiple audio transducers in close proximity to one another, also known as an audio transducer array, or microphone array. While the audio canceling devices may be configured to perform relatively basic signal processing on the received audio signals, in some instances these audio canceling devices might not be equipped with the computational resources necessary for performing certain operations. For instance, the audio canceling devices might not include sufficient computational resources for identifying direction(s) of undesired audio sources to determine an undesired audio source location, for tracking a user or other audio source through the environment and/or for determining a canceling location at which a user may be present.

In one example, an audio canceling device within the environment may receive multiple audio signals, each audio signal received with one of the audio transducers of an audio transducer array of the audio canceling device. The audio canceling device may then send the received audio signals over a network to a distributed computing platform. Upon receiving the multiple audio signals, computing resources of the distributed computing platform may perform signal processing on the first and second audio signals. For instance, these computing resources may utilize various echo cancellation and/or beamforming techniques to isolate a direction or origin location of each of an undesired audio source (e.g., person talking, television) included in the sent audio signals (referred to herein as the undesired audio source location). The computing resources of the distributed computing platform may thereafter distinguish the desired audio from the undesired audio, generate instructions for tuning the audio transducers to best receive the undesired audio and generate an attenuation-signal for use in canceling out the undesired audio at a canceling location. In some implementations, the computing resources may also determine a time delay that is to elapse before the attenuation-signal should be transmitted from the output so that its arrival at a canceling location will coincide with the arrival of the undesired audio, thereby creating destructive interference and lowering the effective volume of the undesired audio at the canceling location without disrupting the desired audio signal.

The architecture may be implemented in many ways. One illustrative implementation is described below in which a single audio canceling device is placed within a room. However, the architecture may be implemented in many other contexts and situations. For example, the architecture described with respect to FIG. 1 utilizes an audio canceling device in combination with remote computing resources. In other implementations all processing and other aspects described herein may be performed locally on the audio canceling device without use of remote computing resources.

FIG. 1 shows an illustrative audio canceling computing architecture set in an example environment 101 that includes a user positioned at a canceling location 103, an undesired audio source (person talking on phone) positioned at an undesired audio source location 105 and a desired audio source 107. The architecture includes an audio canceling device 109 physically situated in a room of the home, but communicatively coupled over a network 111 to remote computing resources 113. In the illustrated implementation, the audio canceling device 109, which in this example includes a transducer 109(1) (e.g., microphone) is positioned on a table near the undesired audio source location 105, while an output 109(2) (e.g., speaker) of the audio canceling device 109 is mounted to the ceiling in the environment 101 at a position closer to the cancelling location 103.

In other implementations, audio canceling devices may be configured in any variety of manners and positioned at any number of locations (e.g., on walls, in a lamp, beneath a table, under a chair, etc.). For example, an audio canceling device may include all the components in a single unit, or different components may be distributed at different locations and connected via wired or wireless communication. As such, implementations described herein may utilize configurations of audio canceling devices that are different than that described with respect to this FIG. 1. Likewise, more or fewer audio canceling devices may be used with implementations described herein. In addition, audio canceling devices may have any number of audio transducers and/or outputs. Some audio canceling devices may only include one audio transducer, while others may include multiple audio transducers, which may be configured as part of an audio transducer array.

The audio canceling device 109 has an audio transducer and an output to facilitate reception of audio signals and transmission of attenuation-signals. In this example, the audio canceling device 109 includes an audio transducer 109(1) that is part of the main component of the audio canceling device 109 and an output 109(2) located within the environment 101 but remote from the main component of the audio canceling device 109. The audio canceling device 109 may be implemented with or without a haptic input component (e.g., keyboard, keypad, touch screen, joystick, control buttons, etc.) or a display in some instances. In certain implementations, a limited set of one or more haptic input components may be employed (e.g., a dedicated button to initiate a configuration, power on/off, etc.). Nonetheless, in some instances the primary and potentially only mode of user interaction with the audio canceling device 109 is through voice input and audible output. One example implementation of an audio canceling device 109 is provided below in more detail with reference to FIG. 2.

The audio canceling device 109 receives audio signals from sound waves in the environment 101 that are generated, for example, by the desired audio source 107 and an undesired audio source. In some implementations as discussed herein, the audio canceling device 109 may also include an image capture device (e.g., camera) that receives visual cues that the audio canceling device or remote computing resource may use to create an audio signal representative of the undesired audio originating from the undesired audio source location, before the undesired audio is received by a transducer. For example, the audio canceling device 109 may include a video camera that records images of the person talking on the phone. Based on the persons lip and/or facial movements the audio canceling device may create an undesired audio signal representative of the undesired audio originating from the person talking on the phone.

After receiving audio signals and identifying the undesired audio signal, and/or creating an undesired audio signal based on visual cues, the audio canceling device 109 may generate an attenuation-signal that will be amplified and transmitted from the output 109(2) and used to effectively reduce the volume of the undesired audio at the canceling location.

In addition to canceling out undesired audio signals, in some instances, the audio canceling device 109 may periodically scan the environment 101 to determine the surrounding acoustical environment. For example, when there is no detected audio, or the audio is below a predetermined threshold, the audio canceling device 109 may transmit signals, such as ultrasonic signals, specifically designed to characterize the structures within the environment by modeling their reflection patterns. Based on the reflection patterns, the signals and/or other components of the audio canceling device, such as one or more of the audio transducers, may be adapted to better characterize the environment and receive audio signals from the environment. For example, reflection patterns may be utilized by the audio canceling device 109 to perform a scan to approximate the dimensions of the environment, the location of objects within the environment, and the density of the objects within the environment. In some instances, multiple audio canceling devices may coordinate or otherwise share information gained from periodic scans of the environment. Such information may be helpful in performing audio cancellation or other functions as described herein. For example, based on reflection patterns the audio canceling device may identify reflections of undesired audio signals that may reach a user positioned at the canceling location and generate attenuation-signals to cancel out those reflections of undesired audio signals.

In some instances, the ambient conditions of the room and/or multiple sources of undesired audio may introduce additional undesired audio signals that form background noise, which increases the difficulty of effectively canceling out undesired audio at a canceling location. In these instances, certain signal processing techniques, such as beamforming, audio source direction and location determination may be utilized in order to identify undesired audio and/or sources of undesired audio. However, in some instances the audio canceling device 109 might not be equipped with the computational resources required to perform the necessary signal processing to identify the undesired audio signal and create an attenuation-signal within an acceptable amount of time after receiving the audio. Therefore, in some instances the audio canceling device 109 may utilize computational capacity of one or more remote computing resources 113 for performing signal processing on audio signals received within the environment 101 to identify the undesired audio signal and create an attenuation-signal for use in canceling out the undesired audio at the canceling location.

The remote computing resources 113 may form a portion of a network-accessible distributed computing platform implemented as a computing infrastructure of processors, storage, software, data access, and other components that is maintained and accessible via a network such as the Internet. Services offered by the resources 113 do not require end user knowledge of the physical location and configuration of the system that delivers the services. Common expressions associated with distributed computing services include "on-demand computing", "software as a service (SaaS)", "platform computing", "network-accessible platform", "cloud-based platform", "cloud computing" and or other similar terms.

The audio canceling device 109 may communicatively couple to the remote computing resources 113 via the network 111, which may represent wired technologies (e.g., wires, USB, fiber optic cable, etc.), wireless technologies (e.g., RF, cellular, satellite, Bluetooth, etc.), and/or other connection technologies. The network 111 carries data, such as audio data, between the audio canceling device 109 and the remote computing resources 113.

As illustrated, in this example the audio signal 115 represents the audio received by an audio transducer of the audio canceling device 109, namely the audio transducer 109(1) of the audio canceling device 109 in this example. This signal 115 represents the audio signal that contains the undesired audio and used for generating the attenuation-signal, as discussed below.

In addition, the audio canceling device 109 may determine a distance between the undesired audio source location 105 and the transducer 109(1), the distance between the transducer 109(1) and the canceling location 103, and the distance between the canceling location 103 and the output 109(2) of the audio canceling device 109. For example, through use of a transducer array the audio canceling device can compute a time offset between audio signals of the undesired audio received by each transducer to determine a location of the undesired audio. A similar technique may be utilized to determine a canceling location 103 when a user at that location initiates the audio canceling device 109 using audio based commands. The location of the output 109(2) may be known and/or can be determined using the same techniques of time offset computation when audio is transmitted from the output.

In order to identify the time offsets between signals received by transducers of the audio canceling device 109, in some instances the audio canceling device 109 compiles each audio signal received by respective audio transducers and then determines the time offsets between the signals by, for instance, using any time-difference-of-arrival ("TDOA") technique, or any other suitable technique. After identifying the respective time offsets, the audio canceling device 109 can determine a direction and/or source location of the audio. In other examples, the audio canceling device 109 may include an image capture device and use images of the environment 101 to determine the undesired audio source location 105, the canceling location 103, the location of the transducer 109(1) and the location of the output 109(2). This information may then be used to compute the distances there between and the time necessary for audio signals to propagate from one location to another (e.g., from the undesired audio source location to the canceling location, from the output to the canceling location, from the undesired audio source location to the transducer).

After identifying the undesired audio source location, the canceling location and the respective distances, the audio canceling device 109 may transmit that information to the remote computing resources 113 for signal processing. In some instances, only the received audio is transmitted. In other instances the location information may also be provided to the remote computing resources 113. In other implementations, rather than utilizing remote computing resources 113, all processing may be done by the audio canceling device 109.

As illustrated, the remote computing resources 113 may include one or more servers, such as servers 117(1), 117(2), . . . , 117(N). These servers 117(1)-(N) may be arranged in any number of ways, such as server farms, stacks, and the like that are commonly used in data centers. Furthermore, the servers 117(1)-(N) may include one or more processors 119 and memory 121, which may store a signal processing module 123. The signal processing module 123 may be configured, for example, to identify undesired audio included in the received audio signal 115 and generate an attenuation-signal for use in cancelling out the undesired audio. In some instances, the signal processing module 123 may use this information to implement beamforming for the audio transducer array within the audio canceling device 109, to provide a response signal 125 back to the environment, and the like. As noted above, the signal processing module 123 may utilize beamforming techniques to focus on audio in a particular area within the environment 102, such as a location corresponding to an undesired audio source location 105.

Figure 2:
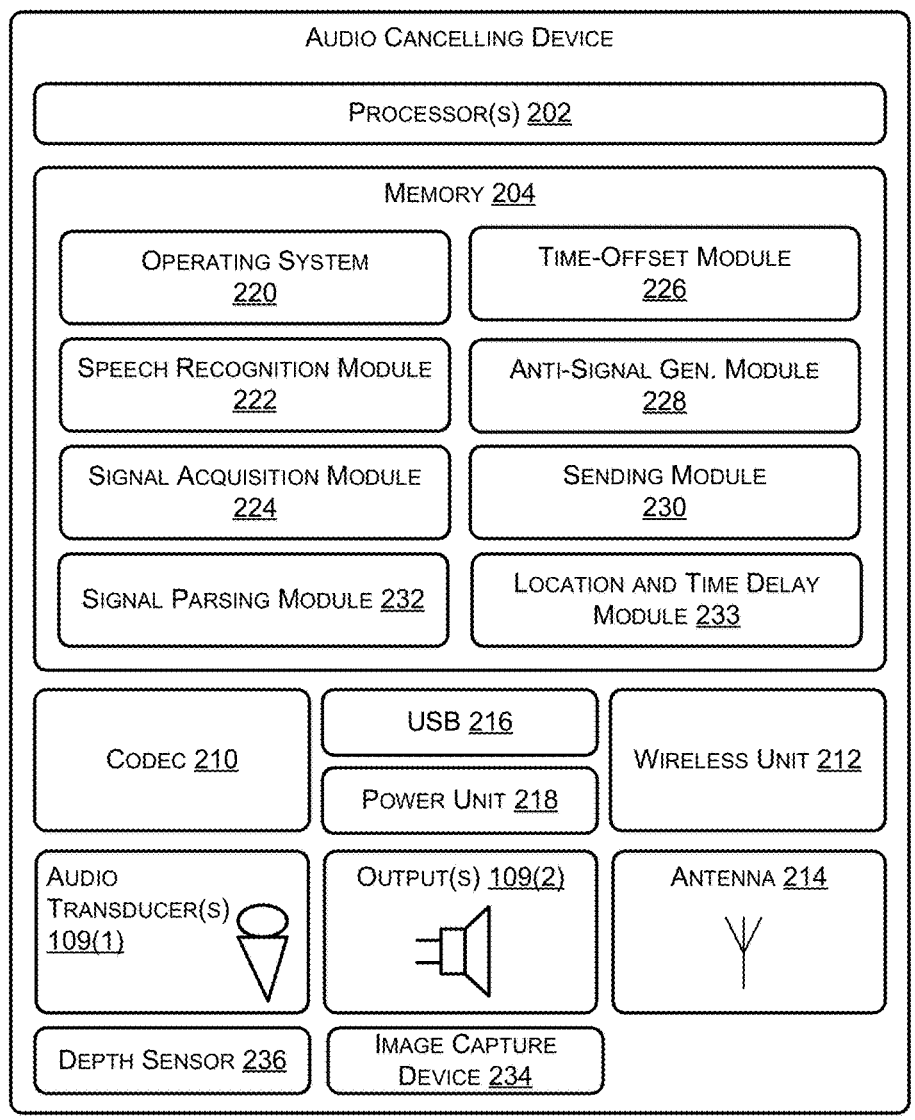
FIG. 2 depicts a block diagram of selected functional components implemented in an example audio canceling device of FIG. 1, including one or more audio transducers for capturing audio and one or more outputs for transmitting audio within the environment.

FIG. 2 shows selected functional components of one audio canceling device 109 in more detail. Generally, the audio canceling device 109 may be implemented as a standalone device that includes a subset of all possible input/output components, memory and processing capabilities. For instance, the audio canceling device 109 might not include a keyboard, keypad, or other form of mechanical input. The audio canceling device 109 might also not include a display or touch screen to facilitate visual presentation and user touch input. Instead, the audio canceling device 109 may be implemented with the ability to receive and output audio, a network interface (wireless or wire-based), power, and processing/memory capabilities.

In the illustrated implementation, the audio canceling device 109 includes one or more processors 202 and memory 204. The memory 204 (and each memory described herein) may include computer-readable storage media ("CRSM"), which may be any available physical media accessible by the processors 202 to execute instructions stored on the memory. In one basic implementation, CRSM may include random access memory ("RAM") and Flash memory. In other implementations, CRSM may include, but is not limited to, read-only memory ("ROM"), electrically erasable programmable read-only memory ("EEPROM"), or any other medium which can be used to store the desired information and which can be accessed by the processors 202.

The audio canceling device 109 may also include one or more audio transducers 109(1) for capturing audio within an environment, such as the example environment 101. In some implementations, the audio transducer 109(1) may take the form of an audio transducer array, such as a microphone array, that includes multiple audio transducers. The audio canceling device 109 may also include one or more outputs 109(2), such as a speaker, to output audio sounds. A codec 210 may couple to the audio transducer(s) 109(1) and output 109(2) to encode and/or decode the audio signals. The codec may convert audio data between analog and digital formats. A user may interact with the audio canceling device 109 by speaking to it, and the audio transducer(s) 109(1) receives the user speech. The codec 210 encodes the user speech and transfers that audio data to other components. The audio canceling device 109 can communicate back to the user by transmitting audible statements through the output 109(2). In this manner, the user interacts with the audio canceling device 109 simply through speech, without use of a keyboard or display common to other types of devices.

The audio canceling device 109 may also include a wireless unit 212 coupled to an antenna 214 to facilitate a wireless connection to a network. The wireless unit 212 may implement one or more of various wireless technologies, such as Wi-Fi, Bluetooth, RF, NFC and other wireless technologies.

A USB port 216 may further be provided as part of the audio canceling device 109 to facilitate a wired connection to a network, or a plug-in network device that communicates with other wireless networks. In addition to the USB port 216, or as an alternative thereto, other forms of wired connections may be employed, such as a broadband connection. A power unit 218 is further provided to distribute power to the various components on the audio canceling device 109.

The audio canceling device 109 may be designed to support audio interactions with the user, in the form of receiving voice commands (e.g., words, phrase, sentences, etc.) from the user, capturing audio from within the environment, identifying undesired audio, generating an attenuation-signal for use in canceling out the undesired audio and transmitting the attenuation-signal in a manner to cancel out or reduce the effective volume of the undesired audio at a canceling location. Accordingly, in the illustrated implementation, there are no haptic input devices, such as navigation buttons, keypads, joysticks, keyboards, touch screens, and the like. Further, there is no display for text or graphical output. There may also be a simple light element (e.g., LED) to indicate a state such as, for example, when power is on, when audio canceling is active, and/or when data is being sent or received.

Accordingly, the audio canceling device 109 may be implemented as an aesthetically appealing device with smooth and rounded surfaces, with some apertures for passage of sound waves, and merely having a power cord, or internal charge (e.g., battery) and communication interface (e.g., broadband, USB, Wi-Fi, etc.). Once plugged in, or otherwise powered, the device may automatically self-configured, or with slight aid of the user, and be ready to use. As a result, the audio canceling device 109 may be generally produced at a relatively low cost. In other implementations, other I/O components may be added to this basic model, such as specialty buttons, a keypad, display, and the like.

The memory 204 may store an array of different datastores and/or modules, including an operating system module 220 that is configured to manage hardware and services (e.g., audio transducer, wireless unit, USB, Codec) within and coupled to the audio canceling device 109 for the benefit of other modules. A speech recognition module 222 may provide speech recognition functionality. In some implementations, this functionality may be limited to specific commands that perform fundamental tasks like waking up the device, selecting a user, canceling an input, activating/deactivating audio canceling, and the like. The amount of speech recognition capabilities implemented on the audio canceling device 109 may vary between implementations, but the architecture described herein supports having speech recognition local at the audio canceling device 109. In alternative implementations, all or a portion of speech recognition may be done using remote computing resources.

The memory 204 may further store a signal acquisition module 224, a time offset module 226, an attenuation-signal generation module 228, a sending module 230, a signal parsing module 232 and a time delay module 233. The signal acquisition module 224 functions to receive signals representing audio signals received by audio transducers of the audio canceling device 109 and optionally from audio transducers of other audio canceling devices within a common environment. For instance, the signal acquisition module 224 may receive the audio signals received by the audio transducer(s) 109(1) of the audio canceling device 109. Likewise, the signal acquisition module 224 may receive audio signals received by audio transducers of other audio canceling device within the environment. In order to receive signals from other audio canceling devices, the audio canceling devices may couple wirelessly, via a wired network, or the like.

After the audio canceling device 109 receives audio signals, the time offset module 226 may determine a time offset between each signal. The time offset module 226 may utilize a TDOA technique, such as cross-correlation to determine time offsets between the signals, or any other technique to determine time offset. The time offset may be used to identify the undesired audio signal location. Similar to speech recognition, determining the undesired audio source location may be done locally by the audio canceling device or through use of remote computing resources.

The signal parsing module 232 may process the audio signal to identify the desired audio and the undesired audio. Several techniques may be used for determining such information. In some instances, the audio canceling device 109 may receive input from the user as to the source of the desired audio (e.g., television). With knowledge of the source of desired audio, the audio canceling device may be communicatively connected to that source and/or have knowledge of the audio being produced by the desired audio source. The audio canceling device 109 can parse the received audio by identifying audio signals that do not correspond with the desired audio (the undesired audio) and generate an attenuation-signal that can be used to cancel out the undesired audio.

In addition, or as an alternative thereto, the audio canceling device 109 may receive input from the user as to the source of the undesired audio (e.g., person talking on the phone, radio). With knowledge of the source of undesired audio, the audio canceling device may be in communication with or otherwise intercept the undesired audio such that it can determine the undesired audio signal. For example, if the undesired audio is a person talking on a wireless home telephone operating at 900 mega-hertz, the audio canceling device may intercept the wireless signal carrying the undesired audio signal and determine the undesired audio signal. Based on the intercepted undesired audio signal, the audio canceling device 109 may generate an attenuation signal for use in canceling out the undesired audio signal at the canceling location.

In other implementations, the audio canceling device 109 may perform speech recognition on the received audio signal using speech recognition module 222 to identify the different audio patterns and sources of audio. Based on the recognized speech, the audio canceling device may then assess which audio source is the desired audio and the undesired audio. For example, if the speech recognition module 222 discerns that one of the audio sources is engaged in a conversation but the other half of that conversation is not included in the received audio, the audio canceling device can predict that the source of that audio is talking on a phone and is thus the undesired audio. In still other implementations, the audio canceling device 109 may include or be communicatively connected to an image capture device 234 (such as a camera). The image capture device 234 may be used to receive the scene of the environment and be used to assist in determining the source locations of the audio. Based on the images of the scene the audio canceling device 109 can predict which audio source is the desired audio and which is the undesired audio. For example, if the audio canceling device 109 receives audio that includes audio from a television and audio from a person talking on the phone, as determined based on images received with the image capture device 234, the audio canceling device 109 may predict that the undesired audio is the person talking on the phone.

In some implementations, if the undesired audio source is generated by a person, the audio cancel device 109 may determine the identity of the person generating the undesired audio signal and/or the speech of the undesired audio signal and selectively cancel or not cancel that undesired audio signal. For example, if the source of the undesired audio signal is the son of the person located at the canceling location, the audio canceling device 109 may not cancel the undesired audio. In addition, there may be specific terms or keywords that, if detected, will result in the audio canceling device 109 not generating an attenuation signal and canceling the undesired audio signal. For example, if the undesired audio includes the word "help" the audio canceling device 109 may not cancel that undesired audio signal at the canceling location.

The memory 204 may also include an attenuation-signal generation module 228 and a time delay module 233. The attenuation-signal generation module 228 receives the undesired audio signal and generates an attenuation-signal by, for example phase shifting and/or inverting the polarity of the undesired audio signal. The location and time delay module may be used to determine the undesired audio source location, the canceling location and, if not already known, the location of the transducer 109(1) and the output 109(2). As noted above, these locations may be computed using any TDOA technique. Likewise, the time delay module 233 may compute a time delay that is to elapse before the attenuation-signal is to be transmitted from an output such that its arrival at the canceling location will coincide with the arrival of the undesired audio.

The speed of sound in air is dependent on the absolute temperature, which directly affects the density of the air. In addition, sound generally propagates through air in an omnidirectional manner. As such, the equation for the speed of sound in air is $c=20.05\sqrt{T}$ (m/s), where T is the absolute temperature of air in degrees Kelvin. At room temperature and standard atmospheric pressure, the speed of sound in air is 343.2 m/s. By utilizing the approximate speed of sound in air of 343.2 m/s and the determined/known locations of the transducer, undesired audio source location, output and cancelling location, the time delay module 233 can determine a time delay that is to elapse before transmitting the attenuation-signal from the output such that the attenuation-signal will arrive at the canceling location at a time that coincides with the arrival of the undesired audio. For example, if the undesired audio source is 10 meters from the canceling location it will take approximately 0.0291 seconds for the undesired audio to travel from the undesired audio source location to the canceling location. Likewise if the distance between the output and the canceling location is 3 meters, it will take approximately 0.00874 seconds for the attenuation-signal to travel from the output to the canceling location. Finally, if the transducer that receives the undesired audio signal is 4 meters from the undesired audio source location, the undesired audio has already traveled for 0.01166 seconds. The time delay may be computed as the difference between the remaining time before which the undesired audio will arrive at the canceling location and the time during which it will take for the attenuation-signal to travel from the output to the canceling location. In this example, the time delay is 0.01919 seconds (0.0291 s.−0.00116 s.−0.00874 s).

In some embodiments, after the audio canceling device 109 determines the undesired audio source location and the canceling location, the sending module 230 may send the received signal and the location information to the remote computing resources 113 for further processing. The sending module 230 may package this data together and/or may provide this data over the course of several communications with the remote computing resources 113.

A depth sensor 236 may also be included in the audio canceling device 109 that may be used alone or in conjunction with other techniques to determine the layout of the environment and/or the location of the user (the canceling location) as well as the undesired audio source location. For example, the depth sensor 236 may transmit and infra-red ("IR") signal (or other modulated light output) and measure a time-of-flight for that IR signal. The time-of-flight value may be derived as a function of a time lapsed between transmission of the IR signal and receive of a returned IR signal that has been reflected by an object within the environment. Alternatively, the time-of-flight value may be derived as a function of the phase difference between the modulated light output and the returned light.

Figure 3:
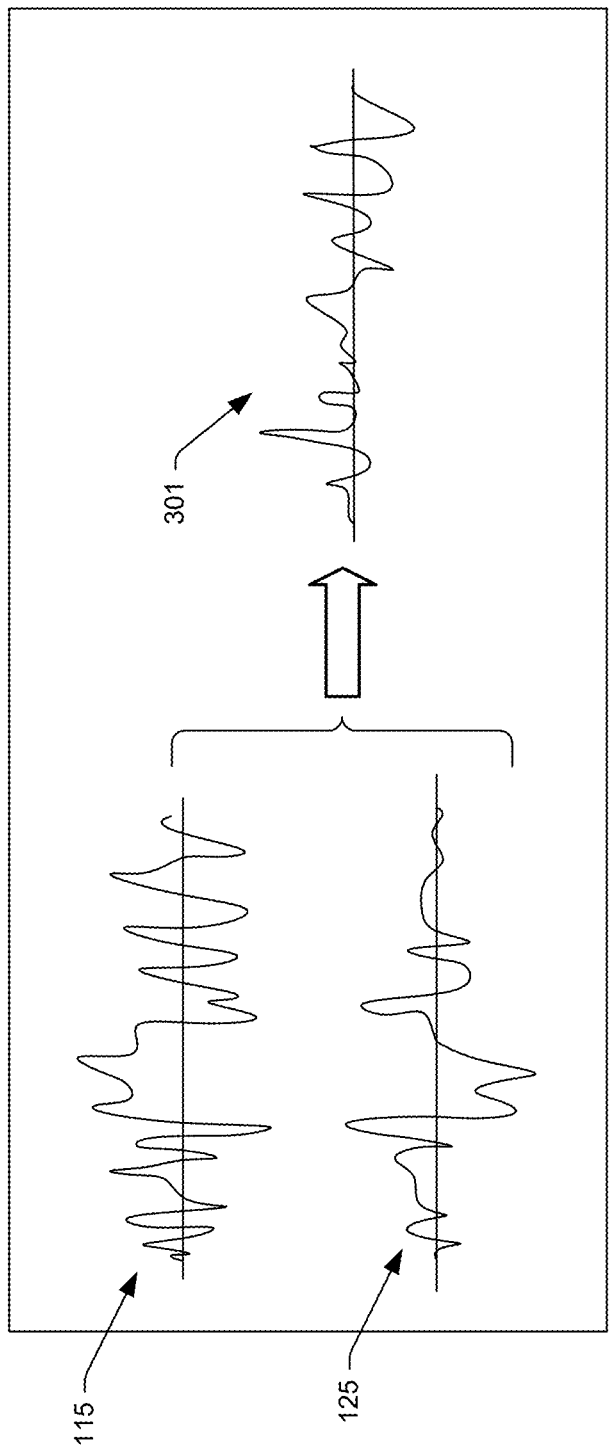
FIG. 3 depicts one possible scenario of combining an audio signal with an attenuation-signal to cancel out undesired audio.

FIG. 3 depicts one possible scenario of combining a received audio signal with an attenuation-signal to cancel out undesired audio. As discussed above, the audio canceling device 109 utilizes a transducer 109(1) to receive audio signal 115 within environment 101 and the signal parsing module 232 parses the received audio signal to identify a desired audio signal and an undesired audio signal. Upon identifying the undesired audio signal the attenuation-signal generation module 228 generates an attenuation-signal 125 and the time delay module 233 determines a time delay that is to elapse before the attenuation-signal is to be transmitted by the output 109(2) such that it will arrive at a canceling location 103 at a time that coincides with the arrival of the sound wave carrying the received audio signals 115. As a result of the sound wave carrying the received audio signal 115 and the sound wave carrying the attenuation-signal 125 arriving at the canceling location, the attenuation-signal causes destructive interference and effectively cancels out or lowers the volume of the undesired audio at the canceling location and leaves the desired audio signal 301 intact.

Figure 4:
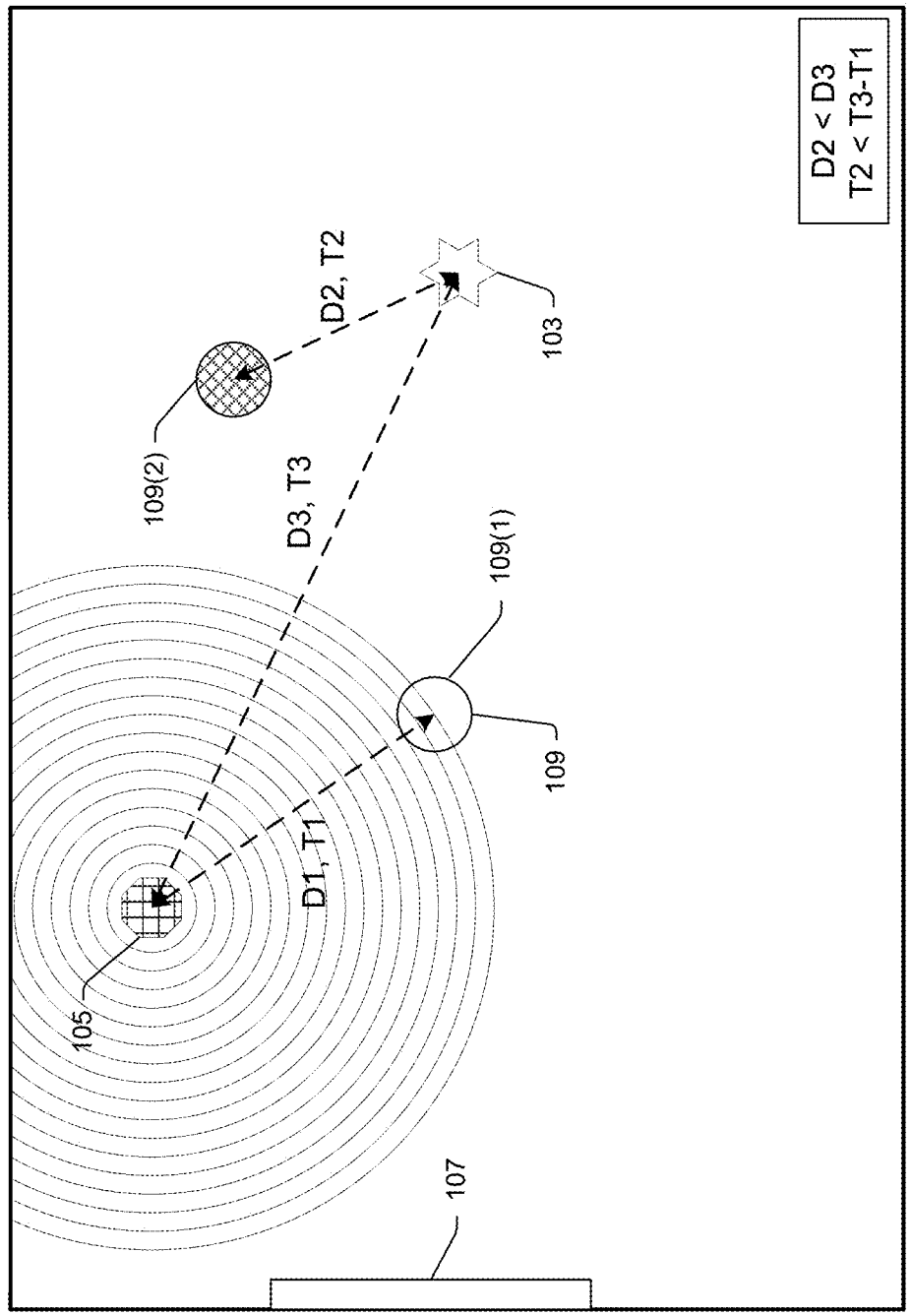
FIGS. 4-6 depict possible scenarios where an implementation of an audio canceling device receives an audio signal and cancels out an undesired portion of that audio signal at a canceling location.
Figure 5:
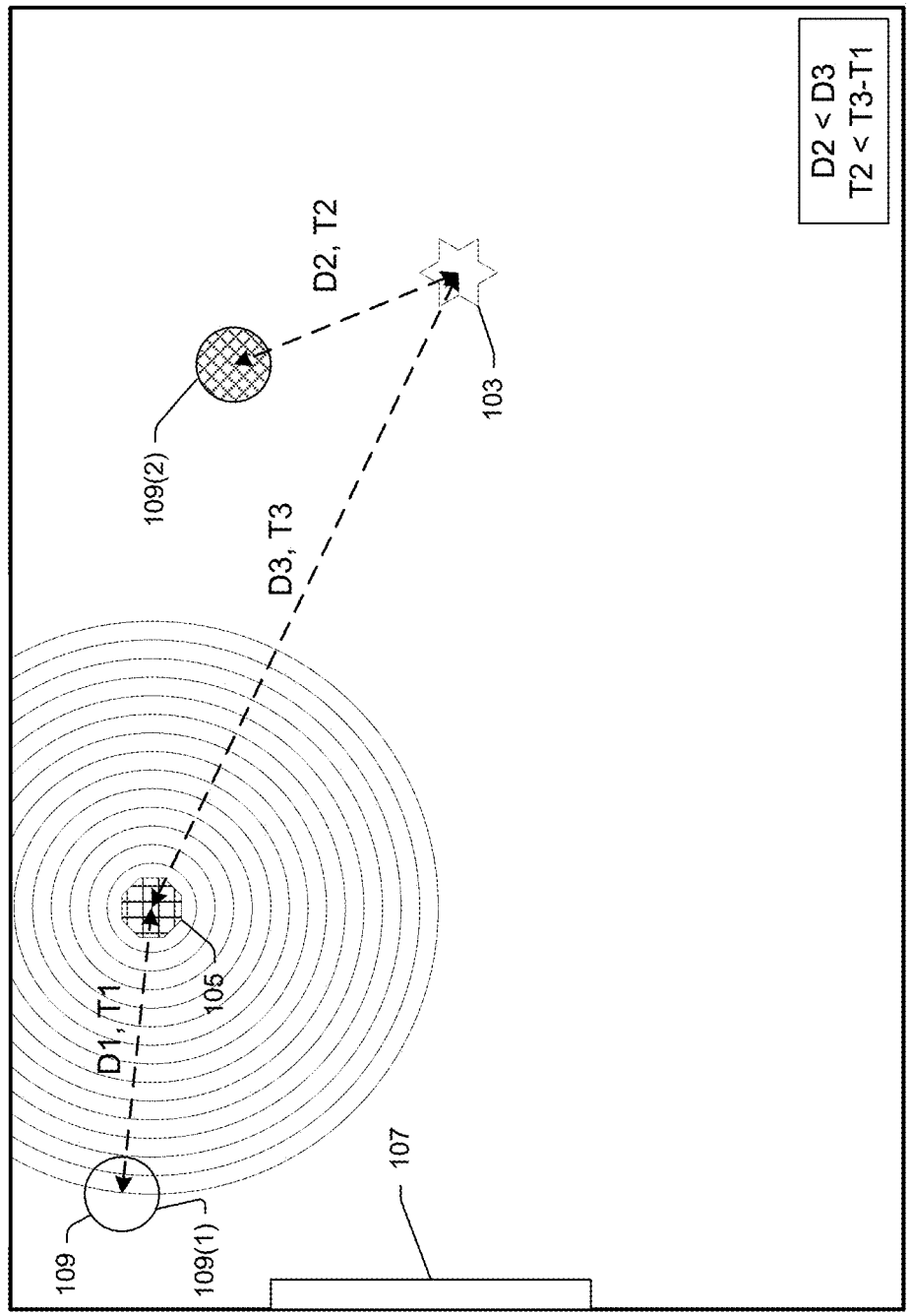
Figure 6:
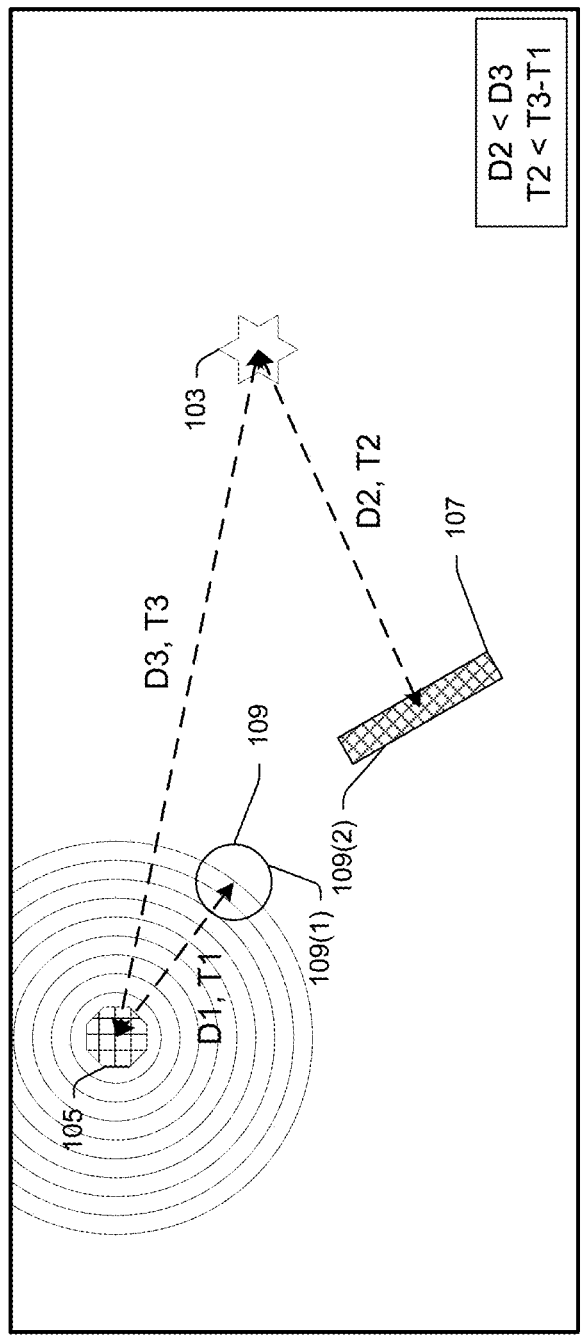

FIGS. 4-6 depict possible scenarios where an audio transducer 109(1) of an audio canceling device 109 in the example environment of FIG. 1 receives an audio signal and cancels out an undesired portion of that audio signal at a canceling location 103. While the scenarios discussed with respect to FIGS. 4-6 utilize an implementation of the audio canceling device in which the transducer 109(1) is located in the audio canceling device 109 and the output 109(2) is positioned within the environment at a location distinct from the audio canceling device 109, it will be appreciated that any configuration of the audio canceling device may be utilized. For example, in other implementations, the transducer may be positioned within the environment at a location distinct from the audio cancelling device. Alternatively, the transducer 109(1) and the output 109(2) may be located within the audio canceling device 109.

As discussed above, an audio transducer 109(1) may receive an audio signal carried by a sound wave within the environment 101 that originates from multiple locations. For example, desired audio may be produced from a desired audio source 107, such as a television. Likewise, undesired audio may be produced from an audio source, such as a person talking on the telephone, positioned at an undesired audio source location 105. Any device, person, entity, or other thing may be identified as producing desired audio and/or undesired audio.

Using the techniques discussed above, upon receiving an audio signal from the environment 101, the audio canceling device 109 identifies the undesired audio source location 105 and the canceling location 103. Utilizing those locations, and the known location of the transducer 109(1) and the output 109(2), the audio canceling device 109 determines the distance D1 between the undesired audio source location 105 and the transducer 109(1), the distance D2 between the canceling location 103 and the output 109(2), and the distance D3 between the undesired audio source location 105 and the canceling location 103. Based on the distances D1-D3 the time intervals T1-T3 that it will take for audio to travel the determined distances are computed and a determination is made as to whether an attenuation-signal may be produced by the output 109(2) that would result in the sound wave carrying the attenuation-signal arriving at the canceling location 103 at a time that coincides with the arrival of the sound wave carrying the undesired audio signal. For example, if the audio canceling device 109 determines that the distance D2 is less than the distance D3 and the time interval T2 is less than the difference between the time intervals T1 and T3, the audio canceling device 109 may determine that an attenuation-signal may be transmitted from the output 109(2) such that the sound wave carrying attenuation-signal will arrive at the canceling location 103 at a time that corresponds with the arrival of the sound wave carrying the undesired audio.

As illustrated in FIG. 4, because the undesired audio source location 105 is farther away from the canceling location 103 than the output 109(2) and the transducer 109(1) is at a location that will allow receipt of the undesired audio signal before it reaches the canceling location 103, the audio canceling device 109 may generate an attenuation-signal and transmit that attenuation-signal from the output 109(2) so that it will arrive at the canceling location 103 at a time that coincides with the arrival of the undesired audio signal.

FIG. 5 illustrates another scenario of the environment 101 that will enable the audio canceling device 109 to effectively cancel out the undesired audio that is originating from the undesired audio source location 105. In this example, even though the transducer 109(1) is not between the undesired audio source location 105 and the canceling location 103, it will still receive the sound wave carrying the undesired audio signal at a time that allows it to generate an attenuation-signal and transmit that attenuation-signal from the output 109(2) such that it will arrive at the canceling location 103 at a time that coincides with the arrival of the sound wave carrying the undesired audio signal, thereby effectively canceling out the undesired audio signal without disrupting the desired audio signal. In the example illustrated in FIG. 5, like FIG. 4, the distance D2 between the output and the canceling location is less than the distance the D3 between the undesired audio source location 105 and the canceling location 103. Likewise, the time interval T2 that it will take for the attenuation-signal to travel from the output 109(2) to the canceling location is less than the difference of the time interval T3 (time interval for the undesired audio to travel from the undesired audio source location to the canceling location) and T1 (time interval for the undesired audio to travel from the undesired audio source location to the transducer).

FIG. 6 illustrates yet another example of the environment 101 in which the transducer 109(1), undesired audio source location 105, desired audio source location 107, output 109(2), and the canceling location 103 are at different positions within the environment 101. In this example, the distance D2 between the output 109(2) and the canceling location 103 is again less than the distance D3 between the undesired audio source location 105 and the canceling location 103. Likewise, the time interval T2 that it will take for the attenuation-signal to travel from the output 109(2) to the canceling location is less than the difference of the time interval T3 (time interval for the undesired audio to travel from the undesired audio source location to the canceling location) and T1 (time interval for the undesired audio to travel from the undesired audio source location to the transducer). In addition, the desired audio source location 107 is closer to the canceling location 103 than is the undesired audio source location 105. As a result, the attenuation-signal generated by the audio canceling device 109 for use in canceling out the undesired audio at the canceling location 103 may be transmitted from an output included in the desired audio source 107. For example, the desired audio source 107 may be a television that includes speakers and the audio canceling device 109 may use the speakers of the desired audio output source 107 as the output 109(2).

It will be appreciated that the scenarios illustrated in FIGS. 4-6 are merely example scenarios of the transducer 109(1), undesired audio source location 105, canceling location 103, desired audio source location 107, and output 109(2) that may be utilized with the implementations described herein. Many other scenarios may also be utilized that will result in generation and transmission of an attenuation-signal that may be used to effectively cancel out the undesired audio signal at a canceling location 103 within the environment 101. In particular, the implementations described herein may be used to cancel out undesired audio at a canceling location 103 in any scenario in which the distance D2 between the output and the canceling location is less than the distance D3 between the undesired audio source location 105 and the canceling location 103 and the time interval T2 that it will take for the attenuation-signal to travel from the output 109(2) to the canceling location is less than the difference of the time interval T3 (time interval for the undesired audio to travel from the undesired audio source location to the canceling location) and T1 (time interval for the undesired audio to travel from the undesired audio source location to the transducer).

Figure 7:
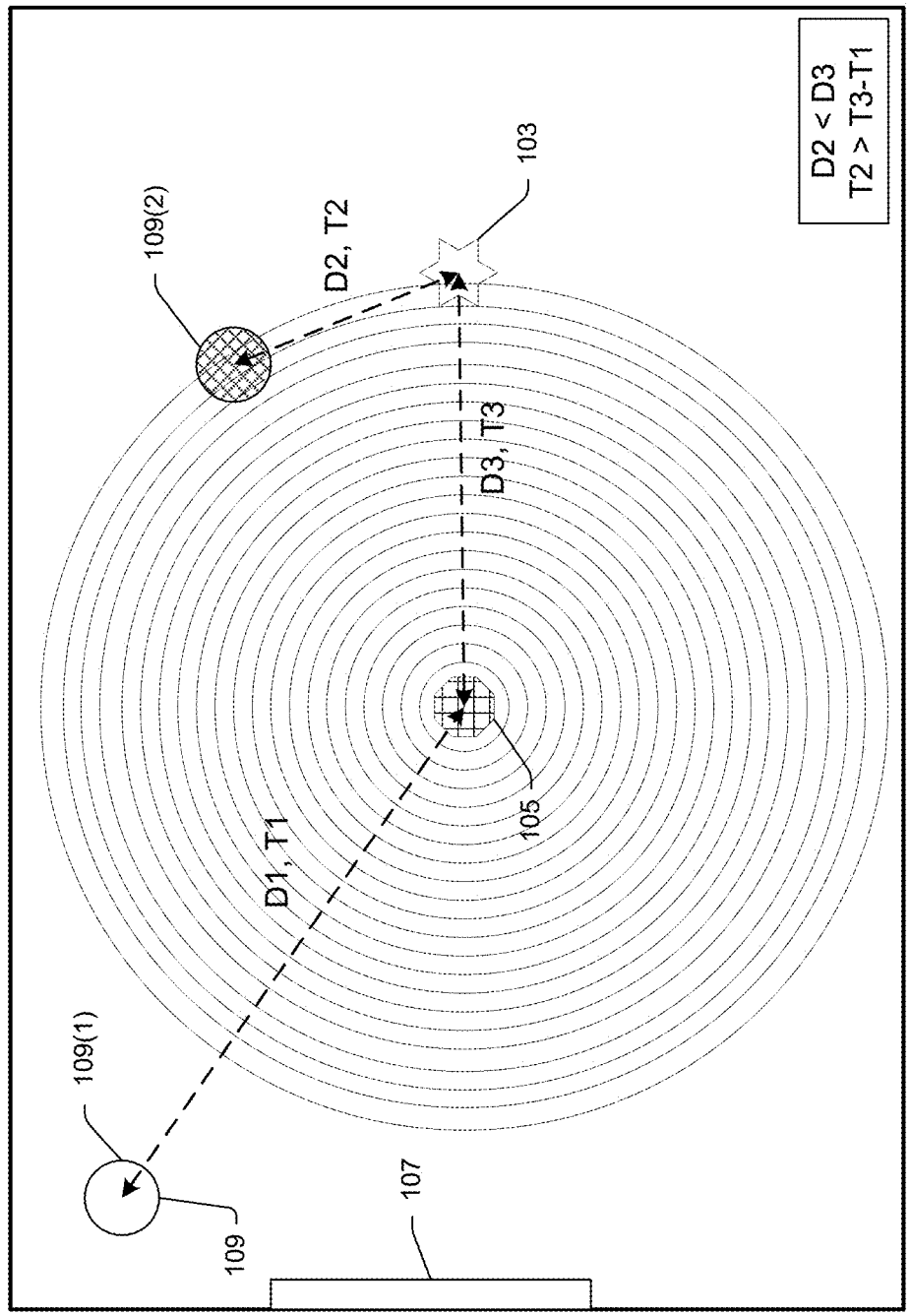
FIGS. 7-8 depict possible scenarios where an implementation of an audio canceling device does not cancel out an undesired portion of an audio signal.
Figure 8:
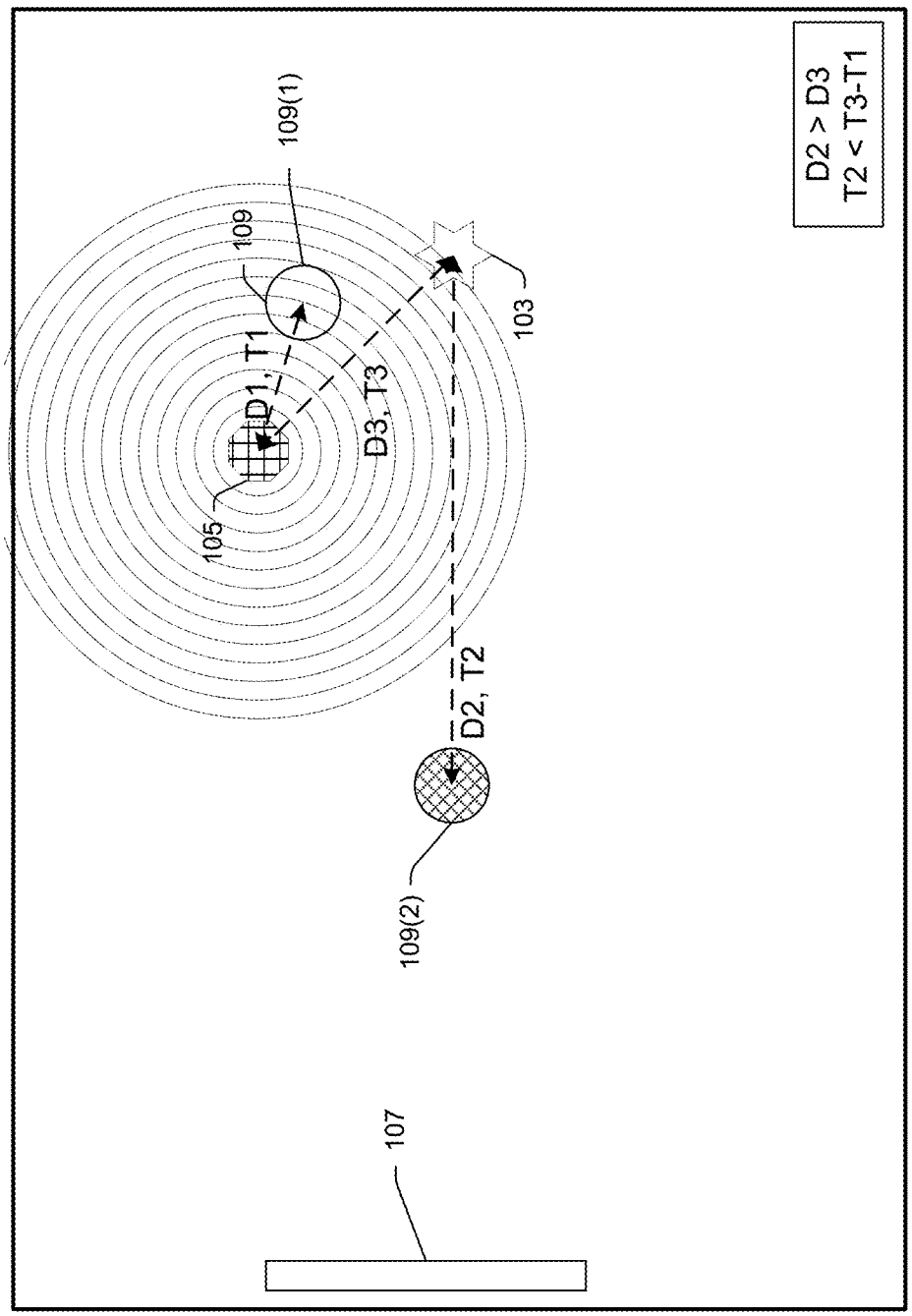

FIGS. 7-8 depict possible scenarios where an audio transducer 109(1) of an audio canceling device 109 in the example environment of FIG. 1 does not cancel out an undesired portion of an audio signal. In the examples illustrated in FIGS. 7-8 the audio canceling device 109 does not utilize an image capture device 234 to create an undesired audio signal representative of the undesired audio originating from the undesired audio source location. However, as described further below, in other implementations the audio canceling device 109 may utilize an image capture device 234 to assist in creating an attenuation-signal for use in canceling out and undesired audio signal in some of the scenarios illustrated in FIGS. 7-8, as well as those illustrated in FIGS. 4-6.

FIG. 7 illustrates an environment 101 in which the time interval T2 that it will take for the attenuation-signal to travel from the output 109(2) to the canceling location is greater than the difference of the time interval T3 (time interval for the undesired audio to travel from the undesired audio source location to the canceling location) and T1 (time interval for the undesired audio to travel from the undesired audio source location to the transducer). Even though the distance D2 between the output 109(2) and the canceling location 103 is less than the distance D3 between the undesired audio source location 105 and the canceling location 103, the sound wave carrying the undesired audio will arrive at the canceling location 103 before it is received by the transducer 109(1) thereby eliminating the ability for the audio canceling device 109 to generate an attenuation-signal that may be transmitted by the output 109(2) for use in canceling out the undesired audio signal at the canceling location.

FIG. 8 illustrates a similar example environment 101 to that of FIG. 7 in which the audio canceling device 109 will not generate an attenuation-signal for use in canceling out undesired audio at the canceling location 103. In this example, the distance D2 to between the output 109(2) and the canceling location 103 is greater than the distance D3 between the undesired audio source location 105 and the canceling location 103. As a result, the attenuation-signal cannot be transmitted in time to arrive at the cancelling location to merge with and cancel the undesired audio signal because the output 109(2) is farther away from the canceling location 103 than is the undesired audio source location 105.

Figure 9:
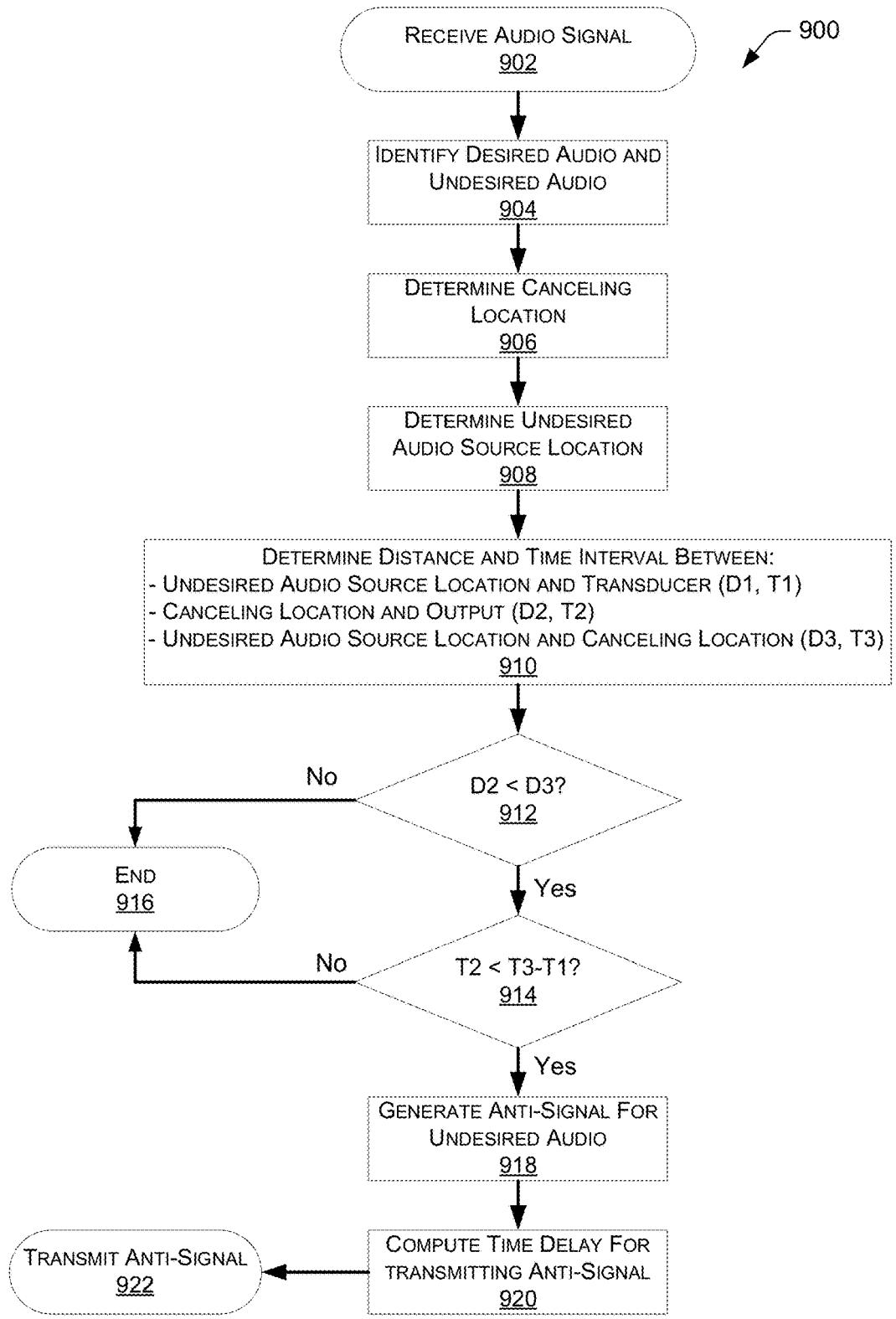
FIG. 9 illustrates a flow diagram of an example process for capturing an audio signal and canceling out undesired audio at a canceling location.

FIG. 9 illustrates a flow diagram of an example process 900 for capturing audio signals within an environment and canceling out undesired audio at a canceling location. This process, and each process described herein, may be implemented by the architectures described herein or by other architectures. The process is illustrated as a series of blocks in a logical flow graph. Some of the blocks represent operations that can be implemented in hardware, software, or a combination thereof. In the context of software, the blocks represent computer-executable instructions stored on one or more computer-readable media that, when executed by one or more processors, perform the recited operations. Generally, computer-executable instructions include routines, programs, objects, components, data structures, and the like that perform particular functions or implement particular abstract data types.

The computer-readable media may include non-transitory computer-readable storage media, which may include hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of storage media suitable for storing electronic instructions. In addition, in some implementations the computer-readable media may include a transitory computer-readable signal (in compressed or uncompressed form). Examples of computer-readable signals, whether modulated using a carrier or not, include, but are not limited to, signals that a computer system hosting or running a computer program can be configured to access, including signals downloaded or uploaded through the Internet or other networks. Finally, the order in which the operations are described is not intended to be construed as a limitation, and any number of the described operations can be combined in any order and/or in parallel to implement the process.

The example process 900 begins upon receiving an audio signal from the environment, as in 902. Upon receiving the audio signal, desired audio and undesired audio are determined, as in 904. As discussed above, there are many techniques that may be utilized for identifying desired audio and undesired audio from the received audio signal. For example, a system implementing the example process 900 may receive input from a user identifying a source of desired audio (e.g., a television). The system may also be communicatively coupled with the source of desired audio and can thereby identify the desired audio from within the received audio signal. The remaining audio signal is therefore the undesired audio.

Regardless of the technique utilized to identify the desired audio and the undesired audio from within the received audio signal, a canceling location is determined, as in 906. The canceling location may be determined by, for example, receiving audio from a user positioned at the canceling location and determining the canceling location by computing a time difference of arrival for the user's audio signal based on when it is received by multiple transducers of a transducer array. Alternatively, an image capturing device may identify the position of the user and use the determined position as the canceling location. In still another implementation, a depth sensor may transmit IR signals to detect the presence of a user at a particular location and identify that as the canceling location. Alternatively, an identifier or other device that will signal a location of the canceling location may be utilized by the user to select a canceling location.

In addition to determining a canceling location, the undesired audio source location is also determined, as in 908. As discussed above, the undesired audio source location may be determined using a variety of techniques. For example, the undesired audio source location may be determined using time difference of arrival of the undesired audio source signal as received by multiple transducers of a transducer array. Alternatively an image capture device may be utilized to identify a location of the source of the undesired audio. In still another implementation, a depth sensor may transmit IR signals to detect the presence of an individual other than the user at a particular location and identify that as the undesired audio source location.

In addition to determining the canceling location and the undesired audio source location, the system implementing the example process 900 may also know or determine the location of the transducer used to receive the audio signals from within the environment as well as a location of the output that may be used to transmit an attenuation-signal. These locations may be already known to the system implementing the example process 900 based on the prior determination of those locations (e.g., during configuration or setup of the audio canceling device). Alternatively, the location of the output may be determined by transmitting an audio signal from the output and using a transducer array to compute a TDOA and determine the location of the output or by identifying the location of the output using an image capture device.

Based on the determined canceling location, undesired audio source location and the locations of the transducer and the output, a distance D1 between the undesired audio source location and the transducer is determined, a distance D2 between the canceling location and the output is determined, and a distance D3 between the undesired audio source location and the canceling location is determined, as in 910. Likewise, time intervals T1-T3 are also computed for each of the distances D1-D3 based on the average speed of sound in air (343.2 m/s), as in 910.

A determination is then made as to whether the distance D2 is less than the distance D3, as in 912. If it is determined that the distance D2 is less than the distance D3 it also determined if the time interval T2 is less than the difference between the time interval T3 and T1 (T2<T3−T1), as in 914. If either the distance D2 is not less than the distance D3 or the time interval T2 is not less than the difference between time intervals T3 and T1 the example process 900 completes and does not generate an attenuation-signal, as in 916. However, if both the distance D2 is less than the distance D3 and the time interval T2 is less than the difference between the time intervals T3 and T1, an attenuation-signal is generated for use in canceling out the undesired audio signal at a canceling location, as in 918. As discussed above, the attenuation-signal may be generated, for example, by phase shifting and/or inverting polarity of the undesired signal. In addition, as noted above, the attenuation signal may be generated locally within the environment or by using remote computing resources. In some embodiments, the example process 900 may determine the time delay (discussed below at 920) and if there is sufficient time to allow for delivery of the received audio signal and potentially other information (e.g., cancelling location, undesired audio source location) to remote computing resources and to receive an attenuation-signal from the remote computing resources, the example process 900 may use the remote computing resources to generate the attenuation-signal. The remote computing resources may have additional processing capabilities that would generate a more representative attenuation-signal than can be generated locally.

In an alternative implementation, the example process may send the received audio and optionally other information to remote computing resources for generation of an attenuation signal and also locally generate an attenuation signal. In such an implementation, if the attenuation signal generated by the remote computing resources is returned before expiration of the time delay, the returned attenuation signal may be used. If the attenuation signal from the remote computing resources is not returned before expiration of the time delay, the locally generated attenuation signal may be used.

In still another implementation, an attenuation signal may be generated locally for use in canceling the undesired audio signal at the canceling location and the remote computing resources may be used to generate one or more attenuation signals for use in canceling reflected undesired audio. Reflected undesired audio may be undesired audio that is reflected off surfaces in the environment and arrives at the canceling location after the original undesired audio. In this implementation, the undesired audio, information about the environment and the position of the canceling location within the environment, may be provided to remote computing resources. The remote computing resources may use that information to determine the reflected undesired audio signal, to generate one or more reflection attenuation signals and to compute one or more reflection time delays. The reflection attenuation signal is an attenuation signal that may be transmitted from an output such that when it combines with the reflected undesired audio signal it effectively cancels out the reflected undesired audio signal. A reflection time delay is the time delay that is to elapse before the output should transmit the reflection attenuation signal such that the reflection attenuation signal will arrive at the canceling location at a time that coincides with the arrival of the reflected undesired audio signal.

In addition to generating an attenuation-signal, a time delay for transmitting the attenuation-signal from an output is computed. As discussed above, the time delay may be computed as the difference between the time interval T3 and T1. At the end of the time delay, the example process 900 transmits the attenuation-signal from an output such that the sound wave carrying the attenuation-signal and the sound wave carrying the undesired audio signal arrive at a canceling location at approximately same time thereby merging and effectively canceling out the undesired audio signal and leaving the desired audio signal intact, as in 922.

In addition to canceling out the undesired audio at the canceling location, in some implementations, the example process 900 may also determine reflected undesired audio that may arrive at the canceling location and generate attenuation-signals that are transmitted such they arrive at the cancelling location at a time that corresponds with the reflected undesired audio signals.

Figure 10:
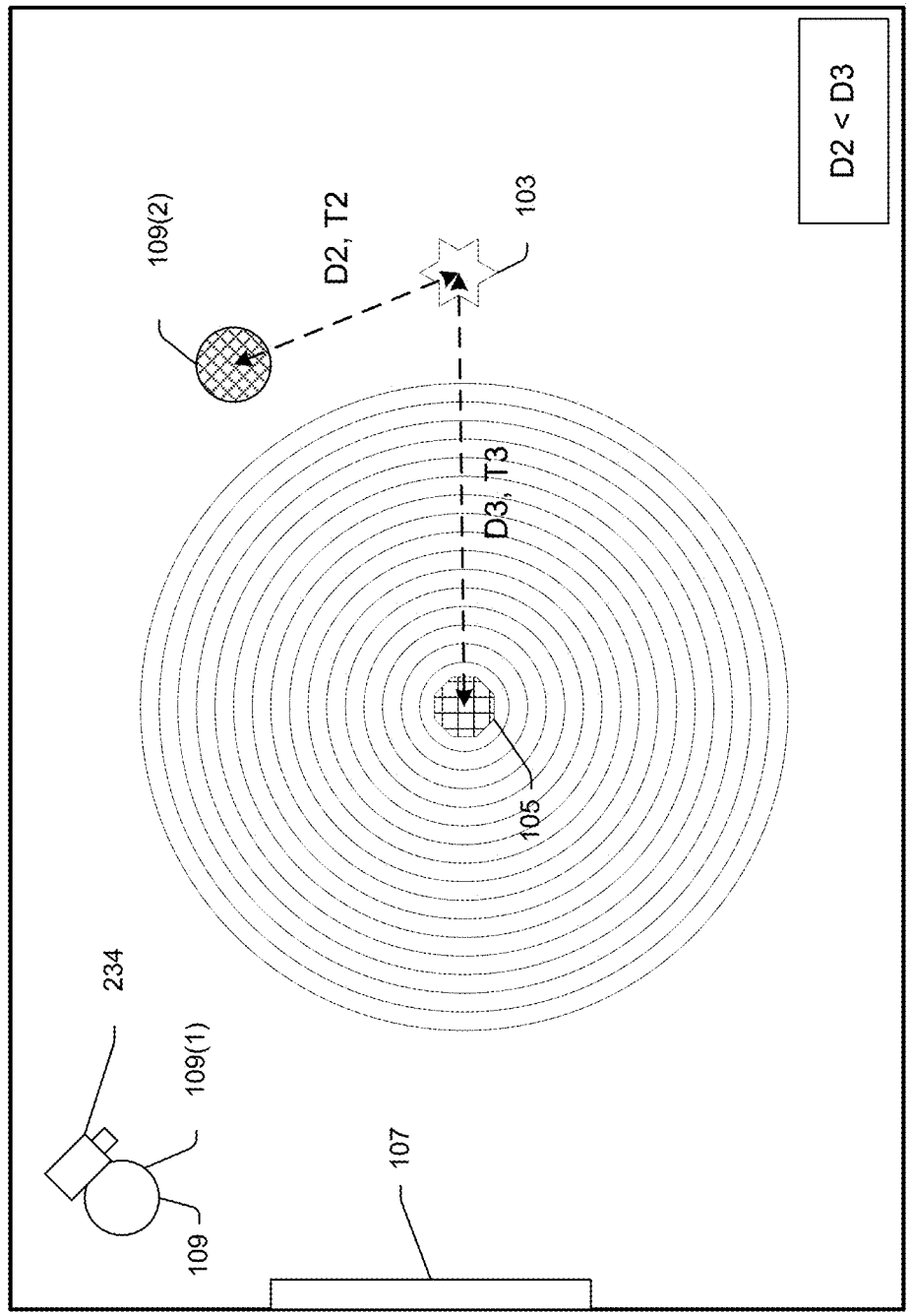
FIG. 10 depicts a possible scenario where an implementation of an audio canceling device receives an audio signal and cancels out an undesired portion of that audio signal at a canceling location.

FIG. 10 depicts a possible scenario where an implementation of an audio canceling device receives an audio signal and cancels out an undesired portion of that audio signal at a canceling location. The audio canceling device 109 operating within the environment 101 may include or be in communication with an image capture device 234. The image capture device 234 may be positioned to receive images of the source of the undesired audio positioned at the undesired audio source location 105. For example, if the undesired audio is originating from a person talking on a telephone, the image capture device 234 may record that person talking on the telephone and predict the audio being generated by that person. For example, the audio canceling device 109 may use visual information gained from the captured images (e.g., movement of a person's lips, mouth and tongue) to determine the undesired audio being produced by the person talking on the telephone and thereby create an undesired audio signal representative of the undesired audio originating from the undesired audio source location 105, before the undesired audio is received at a transducer 109(1).

Alternatively or in addition thereto, the audio canceling device 109 may develop a repository of audio generated by particular individuals and the facial movements that correspond with those audio signals and use that repository to predict the audio being generated by the person talking on the telephone. By creating, rather than receiving the undesired audio being produced at the undesired audio source location 105, the audio canceling device 109 may generate a corresponding attenuation-signal for transmission from an output 109(2) without having to actually receive the undesired audio signal at a transducer 109(1). In this implementation, only the distance between the output 109(2) and the canceling location 103 need be less than the distance between the undesired audio source 105 and the canceling location 103. The time difference can effectively be computed as the time interval between the undesired audio source location and the canceling location because the speed of light (299,792,458 m/s)—the images received by the image capture device 234—is faster than the speed of sound (343.2 m/s). Thus, the attenuation-signal may be generated and transmitted from the output 109(2) so that it will arrive at the canceling location 103 at a time that coincides with the arrival of the sound wave carrying the undesired audio.

The scenario described with respect to FIG. 10 is only an example scenario that may be used with implementations of the audio canceling device 109 that include or communicate with an image capture device 234. Any scenario of the audio canceling device 109, transducer 109(1), output 109(2), undesired audio source location 105, canceling location 103, and the image capture device 234 may be utilized with implementations described herein provided that the distance D2 between the output 109(2) and the canceling location 103 is less than the distance D3 between the undesired audio source location 105 and the canceling location 103 and the audio canceling device 109 can predict the undesired audio as it is being produced from the undesired audio source location 105.

Figure 11:
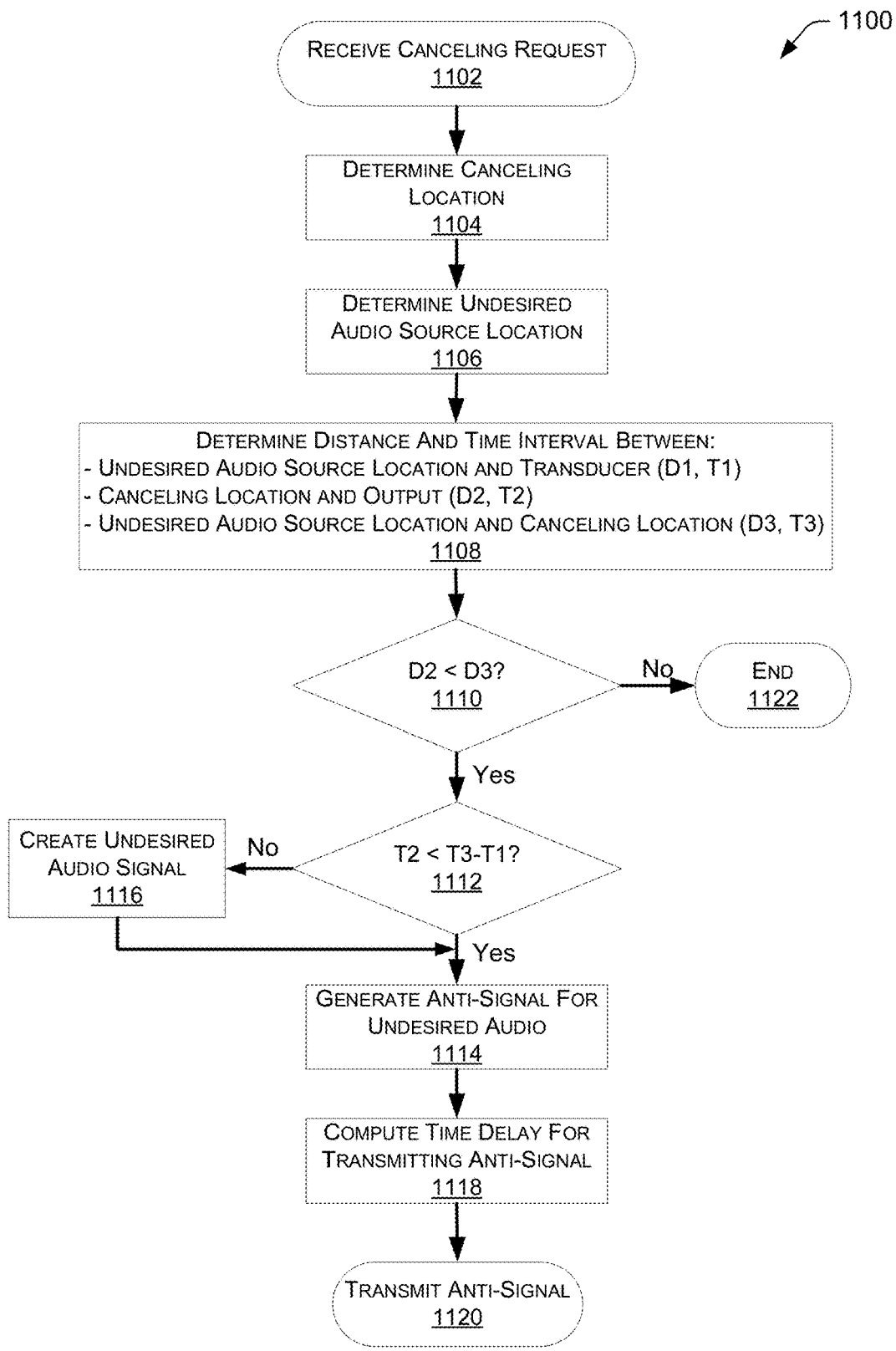
FIG. 11 illustrates a flow diagram of an example process for capturing an audio signal and canceling out undesired audio at a canceling location.

FIG. 11 illustrates a flow diagram of an example process 1100 for capturing an audio signal and canceling out undesired audio utilizing an audio canceling device that includes or is in communication with an image capture device. The example process 1100 begins upon receipt of a canceling request, as in 1102. A canceling request may be received, for example, from a user positioned at the canceling location or from other sources.

Upon receiving a canceling request, a canceling location is determined, as in 1104. The canceling location may be determined using any of the techniques discussed above and/or by determining the location of the user through use of an image capture device. In addition to determining a canceling location, the example process 1100 determines the undesired audio source location, as in 1106. In this implementation, the undesired audio source location may be determined using the image capture device to identify a person within the environment that is producing undesired audio, or by receiving audio from the undesired audio source, or both.

Based on the determined canceling location and determined undesired audio source location, the example process 1100 determines a distance D1 between the transducer and the undesired audio source location, a distance D2 between the canceling location and an output and a distance D3 between the undesired audio source location and the canceling location, as in 1108. As discussed above, the location of the output may already been known to the system implementing the example process 1100, may be determined by transmitting an audio signal from the output or by identifying a location of the output based off an image recorded by an image capture device. Likewise, time intervals T1-T3 are also computed for each of the distances D1-D3 based on the average speed of sound in air (343.2 m/s), as in 1108.

A determination is then made as to whether the distance D2 is less than the distance D3, as in 1110. If it is determined that the distance D2 is less than the distance D3 it also determined if the time interval T2 is less than the difference between the time interval T3 and T1 (T2<T3−T1), as in 1112. Similar to the process described with respect to FIG. 9, if it is determined that both the distance D2 is less than the distance D3 and the difference between the time interval T2 is less than the difference between the time intervals T3 and T1, the example process 1100 may generate an attenuation-signal for use in canceling out the undesired audio signal based on the audio signal received by the transducer. If it is determined that the distance D2 is not less than the distance D3 the example process 1100 completes, as in 1122. In contrast to the example process 900 described with respect to FIG. 9, in the example process 1100 if it is determined that the time interval T2 is not less than the difference between the time intervals T3 and T1, an undesired audio signal is created based on images received using an image capture device, as in 1116. In some implementations, an undesired audio signal may not be created because visual cues are not available. For example, the source of the undesired audio may not be a person or, even if it is a person, the person may not be positioned such that the image capture device can capture the visual cues. In the event that visual cues are not available and an undesired audio signal cannot be created from the captured images, the example process may complete, as in 1122.

Utilizing either the predicted undesired audio or the undesired audio as determined from the audio as received by the transducer, the example process 1100 generates an attenuation-signal for use in canceling out the undesired audio signal at a canceling location, as in 1114. In some embodiments, because the attenuation-signal is based on a created undesired audio signal, the example process 1100 may also include a feedback for use in adjusting the amplitude of the attenuation-signal. For example, as the undesired audio signal is received at a transducer within the environment, the amplitude of the signal may be determine and used to adjust the amplitude of the attenuation-signal if necessary.

In addition a time delay for transmitting the attenuation-signal from an output is determined, as in 1118. Based on the determined time delay the attenuation-signal is transmitted from the output so that the sound wave carrying the attenuation-signal arrives at the canceling location at a time that coincides with the arrival of the sound wave carrying the undesired audio signal, as in 1120.

Although the subject matter has been described in language specific to structural features and methodologies, it is to be understood that the subject matter defined in the appended claims is not necessarily limited to the specific features described. Rather, the specific features are disclosed as illustrative forms of implementing the claims.

What is claimed is:

1. A method comprising:
    under control of one or more computing devices configured with executable instructions,
        generating an attenuation signal based at least in part on an undesired audio signal;
        determining a time interval for the undesired audio signal to travel from a source of the undesired audio signal to an audio canceling device;
        delaying use of the attenuation signal until the time interval has elapsed;
        receiving, at the audio canceling device, the undesired audio signal and a desired audio signal, wherein the desired audio signal includes a user speech of a user that is output by the user while speaking to the audio canceling device;
        subsequent to the time interval having elapsed, using the attenuation signal to at least partially attenuate the undesired audio signal;
        processing, with a speech recognition component of the audio canceling device, the desired audio signal to detect the user speech of the user included in the desired audio signal; and in response to detecting the user speech of the user included in the desired audio signal, supporting an audio interaction between the user and the audio canceling device.

2. The method of claim 1, wherein using the attenuation signal further includes:
subsequent to the time interval having elapsed, using the attenuation signal at the audio canceling device to at least partially attenuate the undesired audio signal as the undesired audio signal is received at the audio canceling device.

3. The method of claim 1, further comprising:
determining at least one of a direction or a location of the source of the undesired audio signal; and
wherein determining the time interval is based at least in part on the direction or the location.

4. The method of claim 1, wherein generating the attenuation signal further includes:
processing, at one or more remote computing resources, an audio signal to determine the undesired audio signal; and
generating, at the one or more remote computing resources, the attenuation signal.

5. The method of claim 1, further comprising:
intercepting, prior to the undesired audio signal arriving at the audio canceling device, the undesired audio signal; and
generating the attenuation signal based at least in part on the intercepted undesired audio signal.

6. The method of claim 1, further comprising:
receiving, from a transducer, at least the undesired audio signal; and
determining, based at least in part on a first location of the transducer and a second location of the audio canceling device, the time interval.

7. The method of claim 1, further comprising:
receiving a request; and
determining, based at least in part on the request, to attenuate the undesired audio signal.

8. An apparatus, comprising:
a transducer;
a processor; and
a memory storing program instructions that, when executed by the processor cause the processor to at least:
obtain an attenuation signal, the attenuation signal generated based at least in part on an undesired audio signal;
determine a time interval for the undesired audio signal to travel from a source of the undesired audio signal to the apparatus;
receive, at the apparatus, the undesired audio signal and a desired audio signal, wherein the desired audio signal includes a user speech of a user that is output by the user while speaking to the apparatus;
subsequent to the time interval having elapsed, use the attenuation signal to at least partially attenuate the undesired audio signal;
processing, with a speech recognition component of the apparatus, the desired audio signal to detect the user speech of the user included in the desired audio signal; and
in response to detecting the user speech of the user included in the desired audio signal, supporting an audio interaction between the user and the apparatus.

9. The apparatus of claim 8, wherein the attenuation signal is obtained from one or more remote computing resources.

10. The apparatus of claim 8, further comprising:
a device operable to determine a distance between the apparatus and the source; and
wherein the program instructions, when executed by the processor, further cause the processor to at least:
determine the time interval based at least in part on the distance.

11. The apparatus of claim 10, wherein the device is at least one of an image capturing device or a depth sensor.

12. The apparatus of claim 8, further comprising:
a transducer array including a plurality of transducers; and
wherein the program instructions, when executed by the processor, further cause the processor to at least:
receive from a first transducer of the transducer array, at least the undesired audio signal; and
determine, based at least in part on a location of the first transducer and a second location at which the undesired audio signal is to be canceled, the time interval.

13. The apparatus of claim 8, wherein the program instructions, when executed by the processor, further cause the processor to at least:
subsequent to the time interval having elapsed, use the attenuation signal to at least partially attenuate the undesired audio signal as the undesired audio signal is received at the apparatus.

14. The apparatus of claim 8, wherein the program instructions, when executed by the processor, further cause the processor to at least:
receive a request; and
determine, based at least in part on the request, that at least a portion of the undesired audio signal is to be attenuated.

15. A computer-implemented method, comprising:
generating an attenuation signal based at least in part on an undesired audio signal;
determining a time interval for the undesired audio signal to travel from a first location to an audio canceling device;
receiving, at the audio canceling device, the undesired audio signal and a desired audio signal, wherein the desired audio signal includes a user speech of a user that is output by the user while speaking to the audio canceling device;
subsequent to the time interval having elapsed, using the attenuation signal to at least partially attenuate the undesired audio signal;
processing, with a speech recognition component of the audio canceling device, the desired audio signal to detect the user speech of the user included in the desired audio signal; and
in response to detecting the user speech of the user included in the desired audio signal, supporting an audio interaction between the user and the audio canceling device.

16. The computer-implemented method of claim 15, wherein using the attenuation signal further includes:
subsequent to the time interval having elapsed, outputting with a speaker of the audio canceling device, the attenuation signal.

17. The computer-implemented method of claim 15, wherein using the attenuation signal further includes:
subsequent to the time interval having elapsed, using the attenuation signal at the audio canceling device to at least partially attenuate the undesired audio signal as the undesired audio signal is received at the audio canceling device.

18. The computer-implemented method of claim 15, wherein generating the attenuation signal further includes:
   processing, at one or more remote computing resources, an audio signal to determine the undesired audio signal; and
   generating, at the one or more remote computing resources, the attenuation signal.

19. The computer-implemented method of claim 15, further comprising:
   determining a distance between the first location and a second location at which the undesired audio signal is to be canceled; and
   wherein the time interval is determined based at least in part on the distance.

20. The computer-implemented method of claim 15, further comprising:
   receiving from a transducer at the first location, at least the undesired audio signal; and
   determining, based at least in part on the first location of the transducer and a second location at which the undesired audio signal is to be canceled, the time interval.

* * * * *